United States Patent
Tai et al.

(10) Patent No.: US 12,110,501 B2
(45) Date of Patent: Oct. 8, 2024

(54) NEUROGENESIS STIMULANT, INTERNAL AGENT, CULTURE MEDIUM ADDITIVE, CELL DILUENT ADDITIVE, CULTURE MEDIUM, AND CELL DILUENT

(71) Applicant: LAIMU CORPORATION, Yokohama (JP)

(72) Inventors: Akihiro Tai, Shobara (JP); Takeru Koga, Shobara (JP); Sachio Wakayama, Yokohama (JP)

(73) Assignee: LAIMU CORPORATION, Kanagawa (JP)

( * ) Notice: Subject to any disclaimer, the term of this patent is extended or adjusted under 35 U.S.C. 154(b) by 798 days.

(21) Appl. No.: 17/057,402

(22) PCT Filed: Nov. 30, 2018

(86) PCT No.: PCT/JP2018/044159
§ 371 (c)(1),
(2) Date: Nov. 20, 2020

(87) PCT Pub. No.: WO2019/225034
PCT Pub. Date: Nov. 28, 2019

(65) Prior Publication Data
US 2021/0207086 A1    Jul. 8, 2021

(30) Foreign Application Priority Data
May 23, 2018   (JP) ................ 2018-098569

(51) Int. Cl.
A61K 31/575    (2006.01)
A61K 31/57     (2006.01)
C12N 5/079     (2010.01)

(52) U.S. Cl.
CPC ............ *C12N 5/0618* (2013.01); *A61K 31/57* (2013.01); *A61K 31/575* (2013.01); *C12N 2501/39* (2013.01); *C12N 2506/45* (2013.01)

(58) Field of Classification Search
CPC .............. A61K 31/575; C12N 2506/45; C12N 5/0618; C12N 2501/39
See application file for complete search history.

(56) References Cited

FOREIGN PATENT DOCUMENTS

| JP | 2001-505058 A | 4/2001 |
|---|---|---|
| JP | 2019-202954 A | 11/2019 |
| WO | 98/24883 A2 | 6/1998 |
| WO | 2006/095798 A1 | 9/2006 |

OTHER PUBLICATIONS

Awad, et al., Beta-sitosterol, a plant sterol, induces apoptosis and activates key caspases in MDA-MB-231 human breast cancer cells, Oncology Reports, 2003, p. 10, pp. 497-500.
Ayaz, et al., Anti-Alzheimer's Studies on Beta-Sitosterol Isolated from *Polygonum hydropiper* L., Frontiers in Pharmacology, 2017, vol. 8, pp. 1-16.
International Search Report and Written Opinion dated Feb. 5, 2019, PCT/JP2018/044159.
International Preliminary Report on Patentability dated Nov. 24, 2020 from corresponding international application No. PCT/JP2018/044159.
Muti, et al., A Plant Food-Based Diet Modifies the Serum beta-Sitosterol Concentration in Hyperandrogenic Postmenopausal Women, J. Nutr., 2003, vol. 133, pp. 4252-4255.
Sayeed, et al., Beta-Sitosterol: A Promising but Orphan Nutraceutical to Fight Against Cancer, Nutrition and Cancer, 2015, pp. 1216-1222, vol. 67(8).
Tachibana, Yoji, Translation of p. 1, Stereoselective Syntheses and Structure-Activity Relationship of Dictyosterol and Related Compounds Exhibiting Neurite Outgrowth, Organizing Committee of 43rd Symposium on the Chemistry of Natural products, Sep. 1, 2001, pp. 1-7.
Tachibana, Yoji, Synthesis and Structure-Activity Relationships of Bioactive Compounds Using Sterols, The Pharmaceutical Society of Japan, 2006, vol. 126(11), pp. 1139-1154.
Office Action dated Feb. 8, 2022 issued in the corresponding Japanese patent application No. 2018-098569 with its English Machine Translation.
Japanese office action dated Jun. 7, 2022, from corresponding Japanese patent application No. 2018-098569.
Office Action dated Sep. 12, 2023 issued in the corresponding Japanese patent application No. 2022-130428 with its English Machine Translation.

*Primary Examiner* — Barbara P Badio
(74) *Attorney, Agent, or Firm* — BROWDY AND NEIMARK, PLLC

(57) ABSTRACT

A neurogenesis stimulant containing a compound having a structure represented by the following formula. $R^1$ to $R^3$ each are an alkyl group having 1 to 10 carbon atoms, and the broken line means presence or absence of a bond.

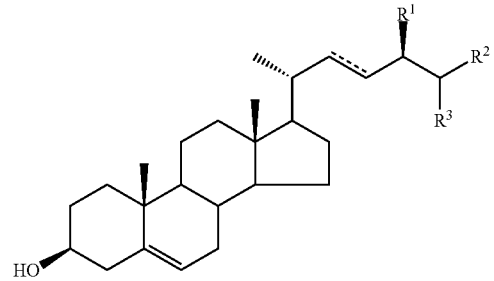

1 Claim, 3 Drawing Sheets

NEUROGENESIS STIMULANT, INTERNAL AGENT, CULTURE MEDIUM ADDITIVE, CELL DILUENT ADDITIVE, CULTURE MEDIUM, AND CELL DILUENT

TECHNICAL FIELD

The present invention relates to a neurogenesis stimulant, and to an internal agent, a culture medium additive, a cell diluent additive, a culture medium and a cell diluent containing the neurogenesis stimulant.

BACKGROUND ART

As human disorders having serious influences on daily life, there are known neurodegenerative diseases such as Alzheimer's disease and Parkinson's disease, as well as nerve damage caused by cerebral ischemia, cerebral contusion or spinal cord injury. Such nervous disorders would detract from cognitive functions and motor functions such as comprehension, memory retention and judgement, and once persons might have such nervous disorders, they could no more readily experience a normal life as drastically changing from the past life. Consequently, developing medicines and medical treatment techniques capable of relieving such nervous function disorders is strongly desired.

Here, those that enable cognitive functions and motor functions in animals such as humans are complicated nerve circuits formed by nerve cell bodies that extend neurites to construct synapses with each other, and it is known that in many nerve diseases, the neurites to form a nerve circuit denature and drop off in the early days. Consequently, for suppressing development of nerve diseases or for relieving symptoms thereof, it is considered to be effective to suppress denaturation of neurites or to administer a substance for promoting formation and extension of neurites for compensating the denatured and dropped neurites. In addition, for recovering the cognitive functions and motor functions impaired by nerve damage, it is also considered to be effective to administer such a substance capable of promoting formation and extension of neurites to reconstruct a nerve circuit. From these points, recently, development of substances capable of promoting formation and extension of neurites is being made and many reports have been made. However, substances capable of promoting formation and extension of neurites that have heretofore been reported are hardly available, or are unsuitable for internal use, or the effect thereof is insufficient, and as it now stands, a neurogenesis stimulant that is highly effective, available at low cost and suitable for internal use is not as yet realized.

On the other hand, the present inventors have paid special attention to β-sitosterol, one type of phytosterol contained in, for example, avocado, soybean, corn or wolfberry fruit. β-sitosterol is known to have a cholesterol metabolizing effect, an antibacterial effect and an anticancer effect (for example, see NPLs 1 to 3). However, the other effects of the substance are not as yet sufficiently clarified, and the use thereof is limited.

CITATION LIST

Non-Patent Literature

NPL 1: Bin Sayeed M. S., Ameen S. S., Beta-Sitosterol: A Promising but Orphan Nutraceutical to Fight Against Cancer. Nutrition and Cancer, 67, 1214-1220 (2015).

NPL 2: Muti P., Awad A. B., Schunemann H., Fink C. S., Hovey K., Freudenheim J. L., Wu Y. W., Bellati C., Pala V., Berrino F., A plant food-based diet modifies the serum beta-sitosterol concentration in hyperandrogenic postmenopausal women. The Journal of Nutrition, 133, 4252-4255 (2003).

NPL 3: Awad A. B., Roy R., Fink C. S., b-sitosterol, a plant sterol, induces apoptosis and activates key caspases in MDA-MB-231 human breast cancer cells. Oncology Reports, 10, 497-500 (2003).

SUMMARY OF INVENTION

Technical Problem

Given the situation, the present inventors have further made investigations about the physiological activity of β-sitosterol from various viewpoints, and have found that β-sitosterol has a strong neurogenesis-stimulating action and is useful as a neurogenesis stimulant. A neurogenesis-stimulating action is an action to promote formation and extension of neurites in nerve cells, and is an action that entirely differs from the heretofore-known effects of β-sitosterol (cholesterol metabolizing effect, antibacterial effect, anticancer effect). Consequently, from these effects, no one can expect that β-sitosterol could have a neurogenesis-stimulating effect.

Accordingly, the present inventors have further made investigations about usefulness of β-sitosterol and compounds analogous thereto as a neurogenesis stimulant, and have further promoted assiduous studies for the purpose of finding out compounds having a strong neurogenesis-stimulating effect and suitable for internal use, and deriving a formula of useful compounds as the neurogenesis stimulant.

Solution to Problem

As a result of assiduous studies made for solving the above-mentioned problems, the present inventors have found that, in addition to β-sitosterol, compounds derived from β-sitosterol by changing the carbon number of the alkyl group bonding to the 17-position of β-sitosterol within a specific range, and compounds derived therefrom by changing the single bond between the 22-position and the 23-position into a double bond also have a neurogenesis-stimulating effect. Utilizing the neurogenesis-stimulating effect of these compounds, the present inventors have found that a neurogenesis stimulant suitable for internal use can be provided at low cost. The present invention has been made on the basis of these findings, and specifically has the following constitution.

[1] A neurogenesis stimulant containing a compound having a structure represented by the following formula (1):

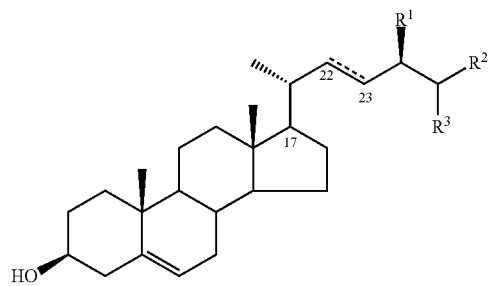

Formula (1)

In the formula (1), $R^1$ to $R^3$ each independently represent an alkyl group having 1 to 10 carbon atoms, and the broken line means presence or absence of a bond.

[2] The neurogenesis stimulant according to [1], wherein $R^1$ in the formula (1) is an alkyl group having 2 to 6 carbon atoms.

[3] The neurogenesis stimulant according to [1] or [2], wherein $R^2$ and $R^3$ in the formula (1) each are an alkyl group having 1 to 6 carbon atoms.

[4] The neurogenesis stimulant according to [1], wherein the compound is β-sitosterol.

[5] The neurogenesis stimulant according to [1], wherein the compound is stigmasterol.

[6] The neurogenesis stimulant according to [1], wherein the compound is campesterol.

[7] The neurogenesis stimulant according to any one of [1] to [6], having an effect of promoting formation of neurites from a nerve body.

[8] The neurogenesis stimulant according to any one of [1] to [7], having an effect of promoting extension of neurites.

[9] The neurogenesis stimulant according to any one of [1] to [8], having an effect of promoting differentiation of stem cells into nerve cells.

[10] The neurogenesis stimulant according to any one of [1] to [9], having an effect of promoting formation and extension of nerve growth factor-inductive neurites.

[11] An internal agent containing the neurogenesis stimulant according to any one of [1] to [10].

[12] A culture medium additive containing the neurogenesis stimulant according to any one of [1] to [10].

[13] A cell diluent additive containing the neurogenesis stimulant according to any one of [1] to [10].

[14] A culture medium containing the culture medium additive according to [12].

[15] A cell diluent containing the cell diluent additive according to [13].

Advantageous Effects of Invention

The compound for use in the present invention has an action of effectively promoting formation and extension of neurites in nerve cells and differentiation of stem cells into nerve cells, and is useful as a neurogenesis stimulant. The internal agent, the culture medium additive, the cell diluent additive, the culture medium and the cell diluent of the present invention contain the neurogenesis stimulant containing the compound of the type, and can therefore effectively express a neurogenesis-stimulating action in living bodies to which the neurogenesis stimulant has been applied.

DESCRIPTION OF EMBODIMENTS

Figure 1:
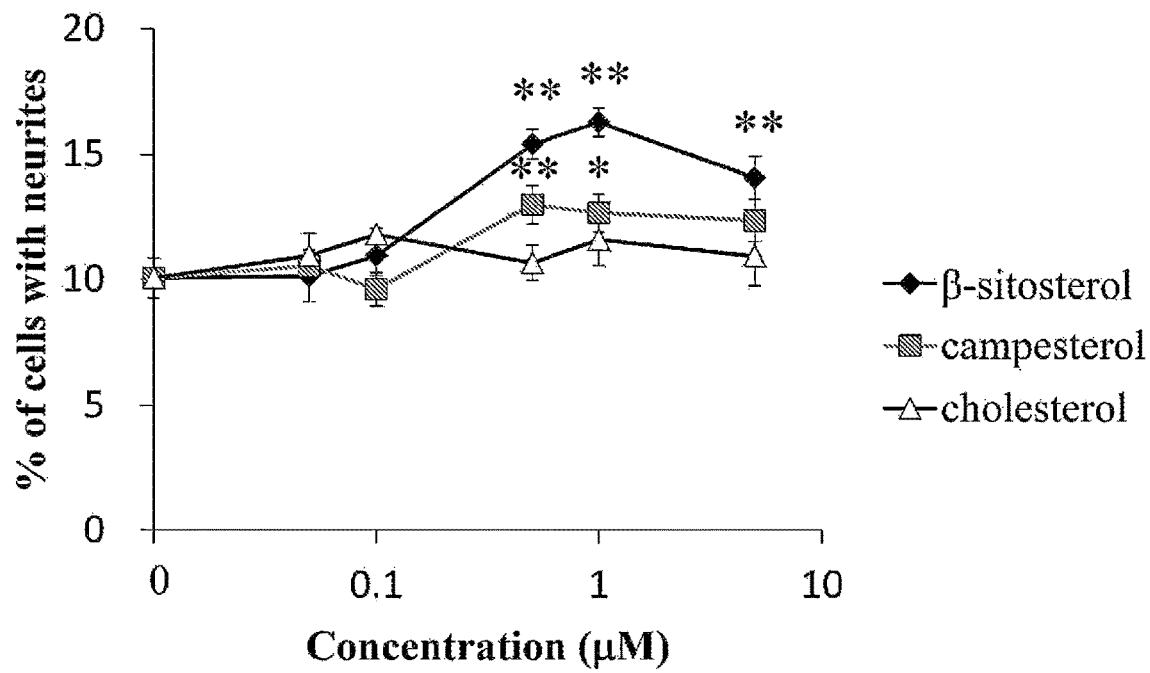
FIG. 1 This is a graph showing a neurite formation ratio in a Bt$_2$cAMP-added PC12 cell culture medium, to which β-sitosterol, campesterol or cholesterol has been added in an amount of 0.05 μM, 0.1 μM, 0.5 μM, 1 μM or 5 μM.

The present invention is described in detail hereinunder. The description of the constitutive elements of the invention given hereinunder is for some typical embodiments or examples of the invention, to which, however, the invention should not be limited. In this description, the numerical range expressed by the wording "a number to another number" means the range that falls between the former number indicating the lower limit of the range and the latter number indicating the upper limit thereof.

[Neurogenesis Stimulant]

The neurogenesis stimulant of the present invention is characterized by containing a compound having a structure represented by the following formula (1):

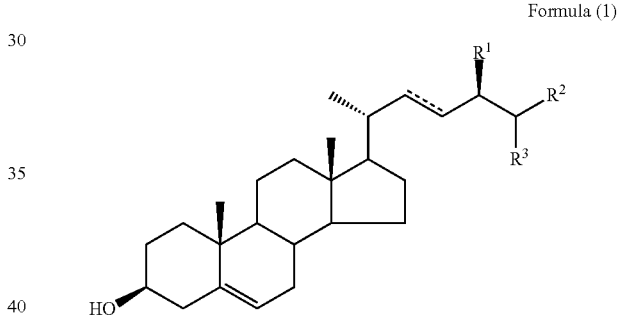

Formula (1)

In the formula (1), $R^1$ to $R^3$ each independently represent an alkyl group having 1 to 10 carbon atoms. The alkyl groups that $R^1$ to $R^3$ represent may be the same as or different from each other. Preferably, $R^1$ to $R^3$ each are an alkyl group having 1 to 6 carbon atoms, and for example, an alkyl group having 1 to 3 carbon atoms can be selected from them. More preferably, $R^1$ is an alkyl group having 2 to 6 carbon atoms. When the carbon number of the alkyl group of $R^1$ is 2 or more, the compound represented by the formula (1) tends to have a stronger neurogenesis-promoting effect. The alkyl group of $R^1$ to $R^3$ may be any of linear, branched or cyclic. Specific examples of the alkyl group include a methyl group, an ethyl group, an n-propyl group and an isopropyl group.

In the formula (1), the broken line to connect the 22-positioned carbon atom and the 23-positioned carbon atom means presence or absence of a bond. In the case of a presence of a bond, the bond between the 22-position and the 23-position is a double bond, and in the case of an absence of a bond, the bond between the 22-position and the 23-position is a single bond. Specifically, the bond between the 22-position and the 23-position may be any of a double bond and a single bond. In any case, the compound represented by the formula (1) exhibits an excellent neurogenesis-promoting effect.

In the following, specific examples of the compound represented by the formula (1) are shown below. However, the compound of the formula (1) usable in the present invention should not be limitatively interpreted by these specific examples.

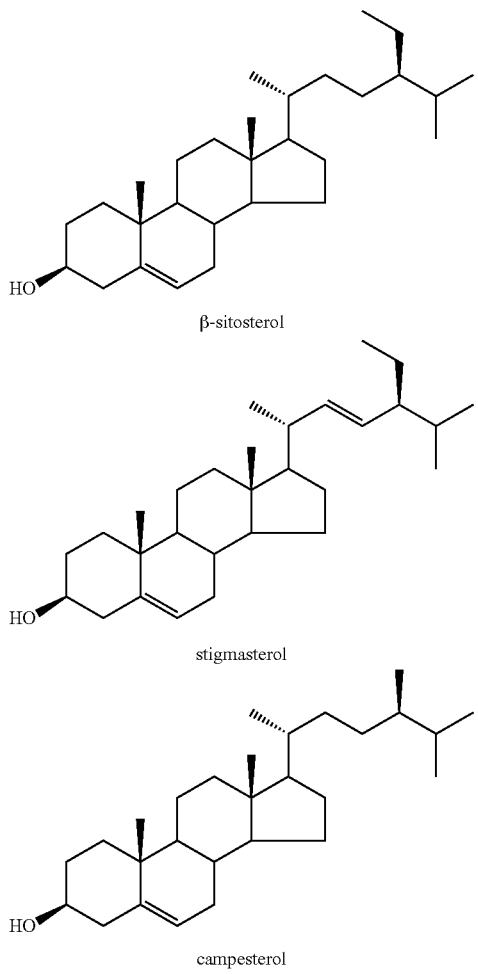

β-sitosterol stigmasterol campesterol

The compound represented by the formula (1) for use in the present invention may be a synthesized one or may also be one extracted from natural sources. For example, the above-mentioned β-sitosterol, stigmasterol, and campesterol are compounds grouped in a phytosterol, and are contained as cell-constituent components in plants. Specifically, β-sitosterol is contained in avocado, soybean, corn, wolfberry fruit and the like, stigmasterol is contained in soybean and the like, and campesterol is contained in canola, corn and the like, and these can be extracted from the plants at a relatively high yield. For extraction of a phytosterol from natural sources, mechanical fragmentation or homogenization of natural sources, hydrolysis thereof with enzyme, acid or base, and various separation and purification methods can be combined. The compound represented by the formula (1) can be produced starting from cholesterol or a cholesterol derivative followed by introducing an alkyl group thereinto by chemical reaction.

In addition to the compound represented by the formula (1), various components may be contained in the neurogenesis stimulant of the present invention. For example, in the case where a vehicle is contained in the neurogenesis stimulant, the blending ratio of the compound represented by the formula (1) and the vehicle can be controlled to adjust the content of the compound of the formula (1) in the neurogenesis stimulant. Though not specifically limited, dextrin is preferred for the vehicle.

The neurogenesis stimulant of the present invention has an effect of promoting formation and extension of neurites in nerve cells (neurogenesis-promoting effect), and, in particular, can effectively promote formation and extension of neurites induced by a nerve growth factor (NGF).

Accordingly, in the case where the neurogenesis stimulant of the present invention is taken orally and where the components thereof are absorbed by the intestinal tract, the stimulant effectively promotes formation and extension of neurites in the nerve system where it has reached to thereby contribute toward reconstruction of the nerve circuit damaged by denaturation or damage of neurites. Accordingly, the neurogenesis stimulant can effectively relieve the disorders of cognitive function and motor function caused by nerve denaturation trouble or nerve damage. Here, the neurogenesis stimulant of the present invention is highly safe since the compound represented by the formula (1) of the active ingredient therein is a phytosterol or a compound analogous to a phytosterol but differing only in point of the carbon number of the alkyl group therein, and therefore has an advantage in that the neurogenesis stimulant can be used as an internal agent to be taken orally with ease.

The neurogenesis stimulant of the present invention has an effect of promoting differentiation of stem cells cultivated in a medium, into nerve cells. Accordingly, the neurogenesis stimulant of the present invention can be effectively used as a differentiation promoter of promoting differentiation of stem cells into nerve cells, in the regenerative medicine area utilizing pluripotent stem cells such as iPS cells or neural precursors. With that, production of nerve cells from stem cells can be attained efficiently, and the neurogenesis stimulant of the present invention can greatly contribute toward production efficiency increase and cost reduction in regenerative medicine-related various industries.

The amount of the neurogenesis stimulant of the present invention to be used varies depending on the targeted failure and, for example, the following dose is preferred.

For example, in the case where the neurogenesis stimulant of the present invention is orally administered as an internal preparation, the dose thereof is preferably 80 to 2000 mg/adult human or mammal standard body weight/day, and multiple dosage of two or three times a day is suitable.

In the case where the neurogenesis stimulant of the present invention is added to a culture medium for cultivating pluripotent stem cells or neural precursors, the concentration of the compound represented by the formula (1) in the culture medium is preferably more than 0.1 μM, more preferably more than 0.2 μM, even more preferably more than 0.4 μM, further more preferably 0.5 μM or more, and is especially preferably 0.5 μM or more and less than 10 μM.

[Use of Neurogenesis Stimulant]

As described above, the neurogenesis stimulant of the present invention has a neurogenesis-promoting effect and has an effect of promoting differentiation of stem cells such as pluripotent stem cells or neural precursors into nerve cells.

Consequently, the neurogenesis stimulant of the present invention can be effectively used as an internal agent which is administered to animals such as human beings to relieve functional disorders thereof caused by neurodegenerative disorders or nerve damages. The neurogenesis stimulant as an internal agent may optionally contain any other various components than the above-mentioned degradation product and vehicle. For example, vitamins, vegetable powders, minerals, yeast extracts, colorants and thickeners may be optionally added thereto. The kind of these components is not specifically limited, and the content thereof may be appropriately controlled within a range capable of sufficiently exhibiting the intended function.

In the regenerative medicine area utilizing pluripotent stem cells such as iPS cells or neural precursors, the neurogenesis stimulant of the present invention may be added to a diluent for a culture medium or cells and can be favorably used as a differentiation promoter of promoting differentiation of such stem cells into nerve cells. The culture medium to which the neurogenesis stimulant is added may be any of liquid (bouillon) media, semi-fluid media, or solid (agar) media, and the composition thereof is not specifically limited. The diluent may be any one ordinary used in the art as a diluent for cells, such as a physiological saline solution, and the neurogenesis stimulant of the present invention is applicable to any of them.

EXAMPLE

The present invention is described more specifically with reference to Example given below. The materials, the ratio thereof, the operations and the like in the following Example may be appropriately varied not overstepping the scope and the spirit of the present invention. Accordingly, the range of the present invention should not be interpreted limitatively by the specific examples shown below.

In this Example, commercially-available β-sitosterol (from Tama Biochemical Co., Ltd.), stigmasterol (from Tama Biochemical Co., Ltd.) and campesterol (from Tama Biochemical Co., Ltd.) were used as compounds represented by the formula (1), and commercially-available cholesterol (from Wako Pure Chemical Industry Co., Ltd.) and progesterone (from Wako Pure Chemical Industry Co., Ltd.) were used as comparative compounds. The structural formulae of the compounds are shown below.

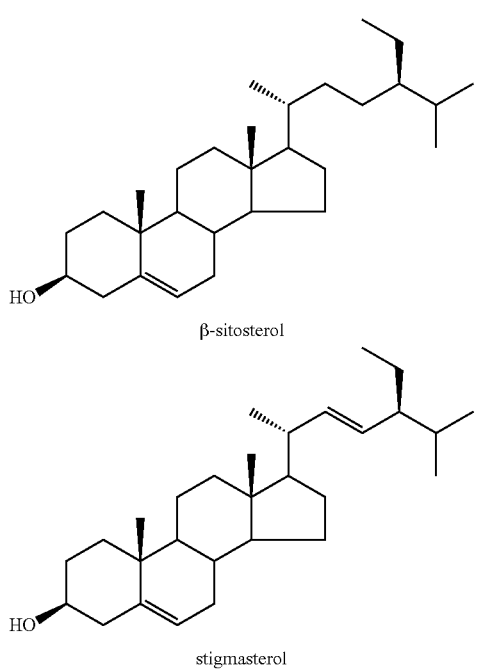

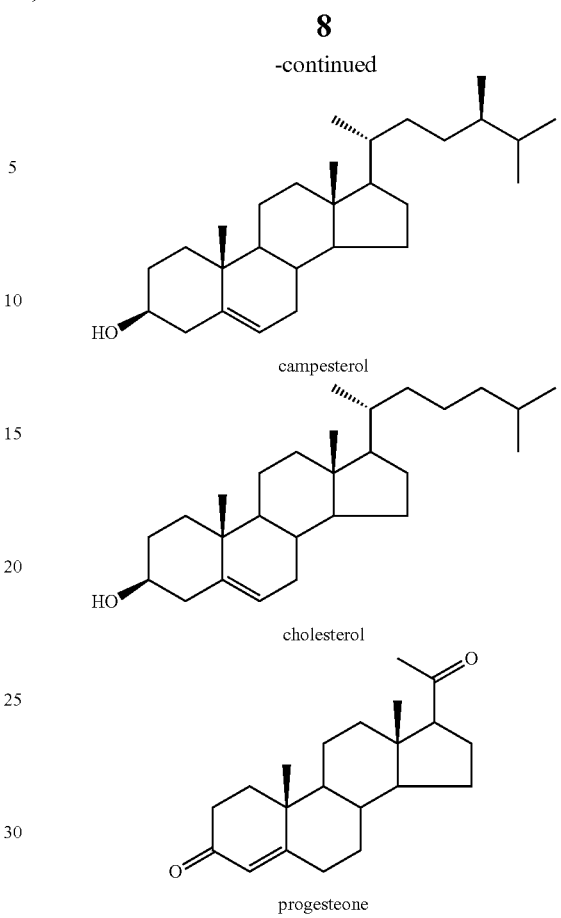

(a) Evaluation of $Bt_2cAMP$-Induced Neurite Formation-Promoting Effect

Using rat adrenal medullary pheochromocytoma-derived PC12 cells (obtained from RIKEN BRC) as a neurodifferentiative model, β-sitosterol, stigmasterol and campesterol were evaluated in terms of the $Bt_2cAMP$ (dibutyryladenosine 3',5'-cyclic monophosphate)-induced neurite formation-promoting effect thereof.

First, PC12 cells were floated on an RPMI-1640 medium (from Sigma Aldrich Corporation) containing 10% equine serum (inactivated), 5% bovine fetal serum (inactivated), 100 U/mL of penicillin G and 100 μg/mL of streptomycin, and well suspended therein so as to be single cells. The suspension of PC 12 cells were sowed on a collagen-coated 96-well plate in an amount of $4.0 \times 10^3$ cells/90 μL/well, and incubated in a 5% $CO_2$ vapor phase at 37° C. for 24 hours. After incubation, a Dulbecco PBS(−) (Dulbecco phosphate buffer physiological saline water not containing Ca and Mg) added with $Bt_2cAMP$ at a concentration of 10 mM, RPMI-1640 medium added with β-sitosterol at a different concentration, or RPMI-1640 medium not added with β-sitosterol was added to the culture medium in each well in an amount of 5 μL each, and further incubated for 24 hours. At that time, the final concentration of each reagent added to the medium in each well was 0.5 mM with no exception for $Bt_2cAMP$, and was 0 μM, 0.05 μM, 0.1 μM, 0.5 μM, 1 μM or 5 μM for β-sitosterol. After incubation, the culture medium was removed from each well, and 1% glutaraldehyde-containing phosphate buffer (0.1 M, pH 7.2) was dispensed in each well in an amount of 100 μL/well, and then left as such for 20 minutes to fix the cells. Subsequently, the glutaraldehyde-containing phosphate buffer was removed from each well, then a Giemsa stain fluid was dispensed in an amount of 100 μL/well, and left as such for 2 to 3 minutes for staining. After staining, the Giemsa stain fluid was removed from each well, and the stained sample in each well was washed twice with ultra-pure water, and then dried.

Thus processed, the sample in each well was observed with a microscope, and the cells with neurites forming in a length of two times the major diameter of the cell body were judged to be positive. The number of the positive cells relative to the total number of cells (the total number of cells judged to be positive or negative) was calculated as percentage to be a neurite formation ratio. Here, for positive or negative judgement, 300 to 400 cells/well were observed.

PC12 cells were incubated according to the same method as above except that stigmasterol or campesterol, or a comparative compound of cholesterol or progesterone was used in place of β-sitosterol, and the neurite formation ratio in each case was calculated.

Figure 2:
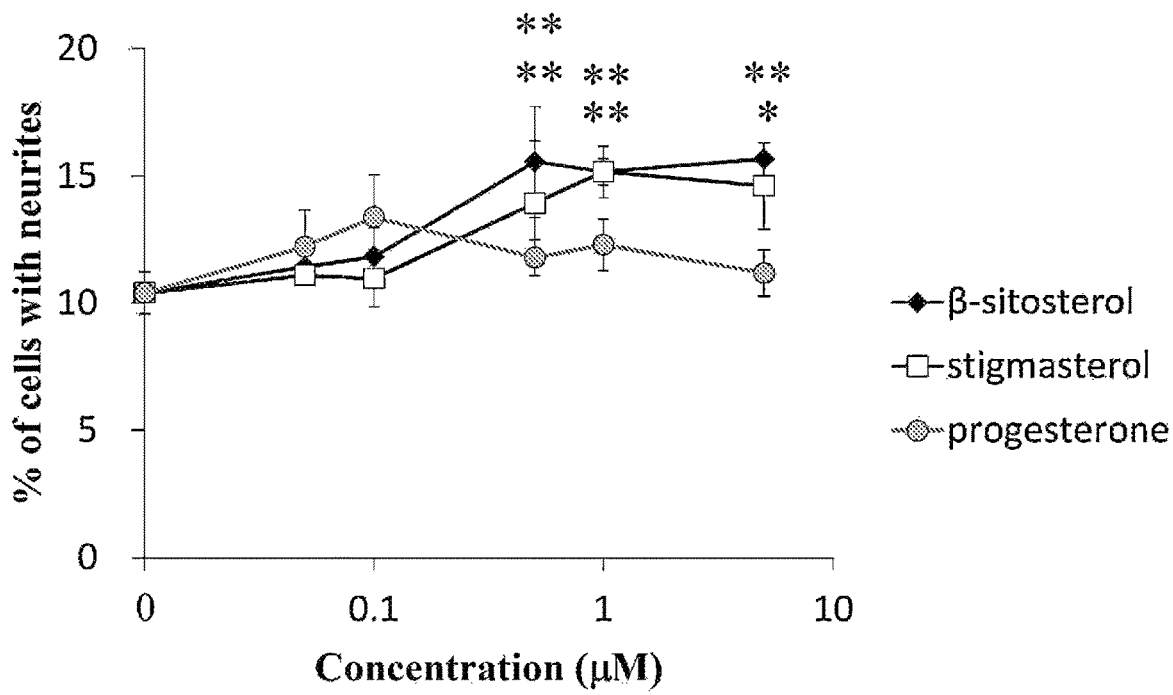
FIG. 2 This is a graph showing a neurite formation ratio in a Bt$_2$cAMP-added PC12 cell culture medium, to which β-sitosterol, stigmasterol or progesterone has been added in an amount of 0.05 μM, 0.1 μM, 0.5 μM, 1 μM or 5 μM.

Graphs were drawn by plotting the neurite formation ratio relative to the concentration of β-sitosterol, campesterol or cholesterol added to the culture medium of PC 12 cells, and shown in FIG. 1. Graphs were drawn by plotting the neurite formation ratio relative to the concentration of β-sitosterol, stigmasterol or progesterone added to the culture medium of PC 12 cells, and shown in FIG. 2. In FIGS. 1 and 2, the horizontal axis is a logarithmic scale. The neurite formation ratio is shown as ±SD, and SD is a standard deviation in the three tests carried out in the same manner. "*" indicates $p<0.05$, and "**" indicates $p<0.01$. The same shall apply to the expression of the neurite formation ratio in FIG. 3, as measured in the following experiment (b).

As shown in FIGS. 1 and 2, in the system added with β-sitosterol, campesterol or stigmasterol, the neurite formation ratio significantly increased owing to the addition of these compounds, in which the neurite formation-promoting effect of these compounds was confirmed. As opposed to these, cholesterol was not recognized to have a neurite formation-promoting effect. Progesterone was recognized to increase the neurite formation ratio when added in an amount of 0.1 μM, but the neurite formation-promoting effect thereof was extremely weak. From these, it is known that the neurite formation-promoting effect of β-sitosterol, campesterol and stigmasterol could not be recognized generally in all sterols and that the effect could be attained only when a specific branched alkyl group is introduced into the 17-position of a specific sterol. In addition, as a result of further investigations relating to structure-activity relationship, β-sitosterol and campesterol that were recognized to have a neurite formation-promoting effect differ from cholesterol not having the effect in point of the group corresponding to $R^1$ in the formula (1), an alkyl group or a hydrogen atom, but the others are the same between the two. This suggests that, for expressing the neurite formation-promoting effect, the alkyl group of $R^1$ is an extremely important factor. Further, the system added with β-sitosterol exhibited a stronger neurite formation-promoting effect than the system added with campesterol, which suggests that the carbon number of the alkyl group to be introduced into $R^1$ is preferably 2 or more. On the other hand, there is no difference in the neurite formation-promoting effect between β-sitosterol where the bond between the 22-position and the 23-position is a single bond and stigmasterol in which the bond therebetween is a double bond, from which it is known that the type of the chemical bond at that position has little influence on the effect, that is, the bond at that position may be any of a single bond or a double bond.

(b) Evaluation of NGF-Induced Neurite Formation-Promoting Effect

Here, NGF (nerve growth factor) differing from $Bt_2cAMP$ in point of signaling pathways was used as an inducing agent for neurite formation to evaluate the NGF-induced neurite formation-promoting effect of β-sitosterol.

Specifically, PC12 cells were incubated according to the same method as above except that an NGF-added Dulbecco PBS(−) was used in place of the $Bt_2cAMP$-added Dulbecco PBS(−) and the incubation time for the PC12 cells after addition of NGF and β-sitosterol thereto was 48 hours, and the neurite formation ratio was calculated. The final concentration of each reagent added to the culture medium of PC12 cells in each well was 10 ng/ml with no exception for NGF, and was 0 μM, 0.05 μM, 0.1 μM, 0.5 μM, 1 μM or 5 μM for β-sitosterol. A graph was drawn by plotting the neurite formation ratio relative to the concentration of β-sitosterol added to the culture medium of PC 12 cells, and shown in FIG. 3.

Figure 3:
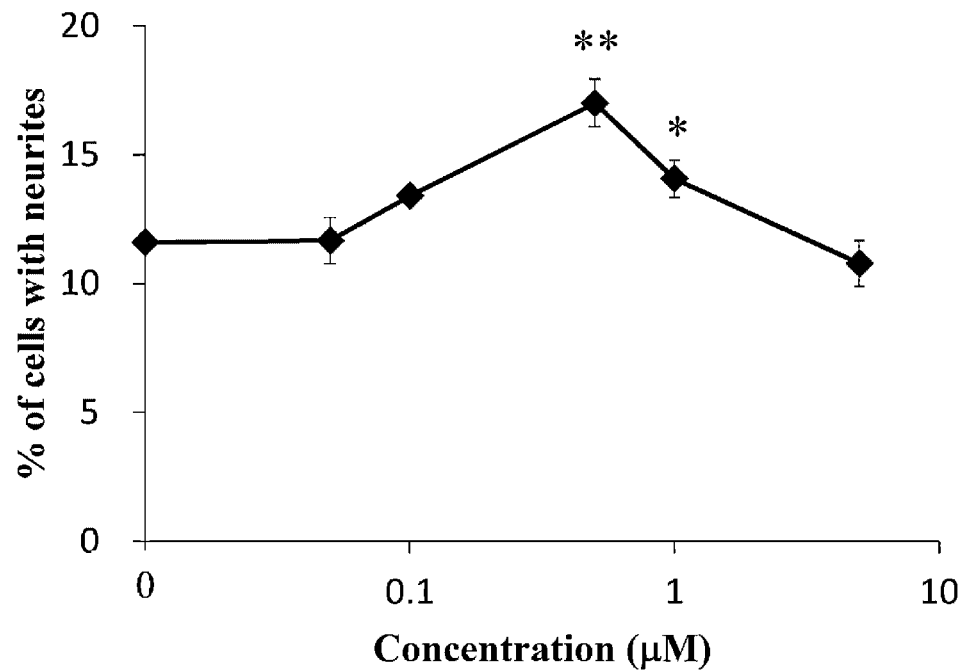
FIG. 3 This is a graph showing a neurite formation ratio in an NGF-added PC12 cell culture medium, to which β-sitosterol has been added in an amount of 0.05 μM, 0.1 μM, 0.5 μM, 1 μM or 5 μM.

From FIG. 3, it is known that, by adding β-sitosterol to the culture medium, the neurite formation ratio significantly increased. From this, it is confirmed that β-sitosterol exhibits the effect of promoting neurite formation under any of $Bt_2cAMP$ induction or NGF induction.

(c) Cell Toxicity Test

For confirming that the neurite formation-promoting effect of each compound recognized in the above-mentioned evaluations (a) and (b) is not caused by stress (cell toxicity) given to cells, the number of living PC12 cells incubated in a culture medium added with $Bt_2cAMP$ and β-sitosterol was evaluated using Calcein-AM (from Dojindo Molecular Technologies, Inc.). Calcein-AM is a cell membrane-permeable compound, and when taken in living cells, it is hydrolyzed with esterase to release calcein. Calcein-AM itself does not almost emit fluorescence, but calcein released through hydrolysis emits strong fluorescence, and is membrane-impermeable. Accordingly, after a group of cells were processed with Calcein-AM so as to make Calcein-AM taken by the living cells, and then the cells were disrupted to measure the fluorescence intensity by calcein, whereby the number of the living cells in the group of cells can be known.

Specifically, under the same condition as that for the above-mentioned evaluation (a), PC12 cells were incubated on a 96-well plate for 24 hours, and then a $Bt_2cAMP$-added Dulbecco PBS(−), and an RPMI-1640 medium added with β-sitosterol or an RPMI-1640 medium not added with β-sitosterol were added to the medium in each well. At that time, the final concentration of each reagent added to the medium in each well was 0.5 mM with no exception for $Bt_2cAMP$, and was 0 μM, 0.05 μM, 0.1 μM, 0.5 M, 1 μM or 5 μM for β-sitosterol. In 24 hours after addition of each reagent, a solution prepared by diluting 100 μM Calcein-AM by 20 times with a Dulbecco PBS(−) was dispensed in each well in an amount of 100 μL/well, and then incubated for 30 minutes. Subsequently, a Dulbecco PBS(−) containing 0.6% of Triton X-100 (from Sigma Aldrich Corporation) was dispensed in each well in an amount of 20 μL/well, stirred at 1000 rpm for 5 minutes, and then the cells were disrupted by application of ultrasonic waves thereto.

Figure 4:
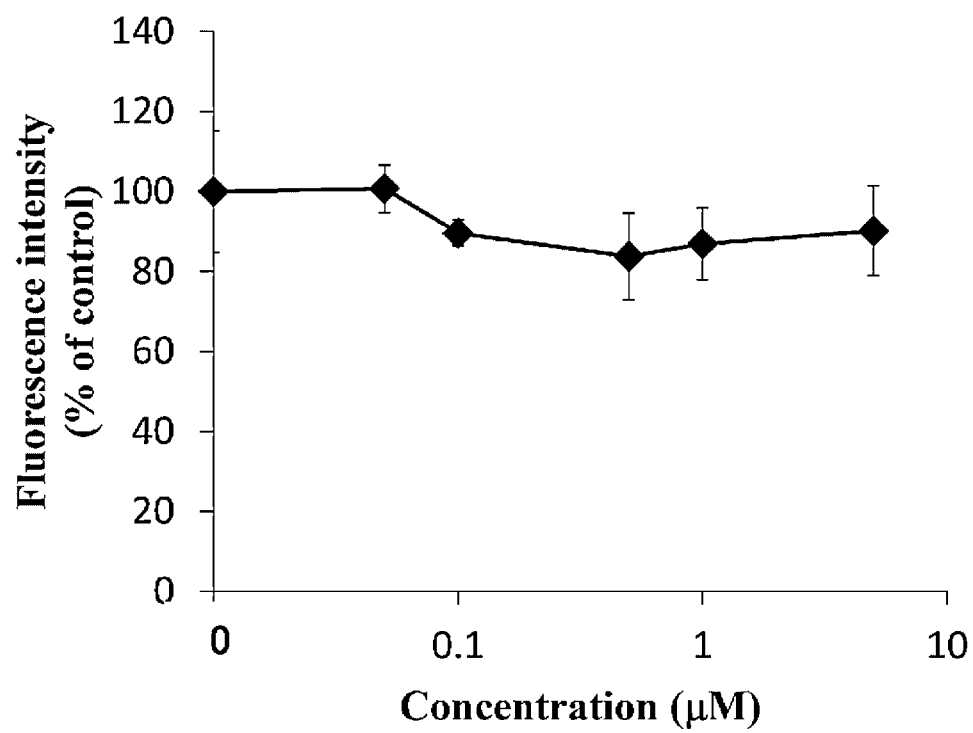
FIG. 4 This is a graph showing results of a cell toxicity test of β-sitosterol.

The fluorescence intensity of the sample in each well processed as above was measured at an excitation wavelength of 485 nm and a detection wavelength of 527 nm. The data of the measured fluorescence intensity were plotted relative to the concentration of β-sitosterol added to the culture medium of PC12 cells, and the resultant graph is shown in FIG. 4. In FIG. 4, the horizontal axis is a logarithmic scale. The fluorescence intensity is a relative value based on the actual value of the fluorescence intensity, 100%, measured in the system not added with β-sitosterol, and is shown as ±DS. SD is a standard deviation of three tests carried out under the same condition.

As in FIG. 4, the fluorescence intensity changed little even when the concentration of β-sitosterol in the culture medium was increased, and it is known that the number of living cells does not decrease when β-sitosterol is added within the concentration range tested in this experiment. From this, it is confirmed that the neurite formation-promoting effect of β-sitosterol is not caused by the stress given to cells but is the activity effect of β-sitosterol.

(d) Evaluation of NGF-Inductive Neural Differentiation-Promoting Effect

A neurofilament was used as a neural differentiation marker. This was stained according to an immunofluorescent staining method for evaluating the neural differentiation promoting effect of β-sitosterol.

PC12 cells were floated in an RPMI-1640 medium containing 10% equine serum (inactivated), 5% bovine fetal serum (inactivated), 100 U/mL of penicillin G and 100 μg/mL of streptomycin and well suspended therein to be single cells of $1.4 \times 10^4$ cells/mL. The suspension of PC12 cells was sown in a collagen-coated 8-well chamber slide at $5.0 \times 10^3$ cells/360 μL/well, and incubated in a 5% $CO_2$ vapor phase at 37° C. for 24 hours. After incubation, an NGF-added Dulbecco PBS(-) (NGF solution), and a β-sitosterol-added RPMI-1640 medium (β-sitosterol solution) were added to the medium in each well in an amount 20 μL/well each, and further incubated for 48 hours. At that time, the final concentration of each reagent added to the medium in each well was 10 ng/ml for NGF, and was 0.5 μM for β-sitosterol. After incubation, the medium was removed from each well, which was then washed with PBS(-) (phosphate buffer physiological saline water (not containing Ca and Mg)), processed with a 4% formaldehyde solution dispensed in each well for 30 minutes, and thereafter washed three times with PBS(-) for 3 minutes. Subsequently, each well was processed with a 0.4% Triton X-100-containing PBS(-) dispensed therein for 5 minutes, and then washed with PBS(-).

Next, a 2.5% bovine serum albumin (BSA)-containing PBS(-) was dispensed in each well to process it for 1 hour, then a primary antibody (anti-neurofilament 200 IgG fraction of antiserum, from Sigma Aldrich Corporation) diluted by 200 times with a 2.5% BSA-containing PBS(-) was dispensed in each well to process it at room temperature for 2 hours, and then washed three times with PBS(-) containing 0.05% Tween 20 (EzTween, from ATTO Corporation) for 3 minutes. Subsequently, a secondary antibody (Anti-Rabbit IgG (whole molecule)-FITC antibody produced in goat, from Sigma Aldrich Corporation) diluted by 200 times with PBS(-) containing 2.5% BSA was dispensed to each well and processed at room temperature for 1 hour, and washed three times with PBS(-) containing 0.05% Tween 20 for 3 minutes. The sample in each well processed in the manner as above was sealed up with a nuclear stain sealant (DAPI-Fluoromount-G, from Cosmo Bio Corporation), covered with a cover glass, and the four sides thereof were manicured to produce a specimen 1.

On the other hand, a comparative specimen 1 was produced according to the same process of incubation and immunofluorescent staining as above, except that Dulbecco PBS(-) was used in place of the NGF solution and an RPMI-1640 medium was used in place of the β-sitosterol solution; and a comparative specimen 2 was produced according to the same process of incubation and immunofluorescent staining as above, except that an RPMI-1640 medium was used in place of the β-sitosterol solution.

Figure 5:
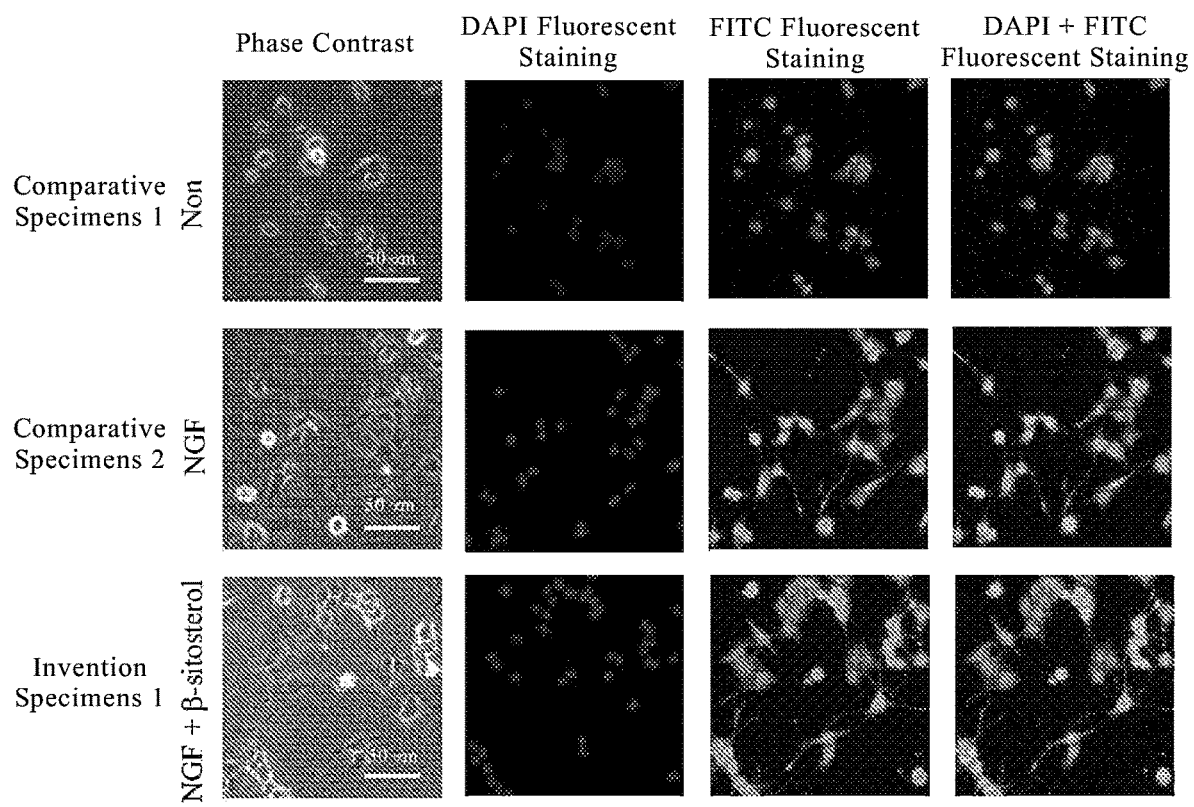
FIG. 5 This shows phase contrast photographs and fluorescently-stained images of PC12 cells incubated in a culture medium not added with NGF or β-sitosterol (comparative specimens 1), PC12 cells incubated in a culture medium added with NGF (comparative specimens 2), and PC12 cells incubated in a culture medium added with NGF and β-sitosterol (invention specimens 1).

A fluorescently-stained picture of each sample was observed and taken using a confocal laser microscope (FLUOVIEWFV10i, from Olympus Corporation). The pictures are shown in FIG. 5. In FIG. 5, the pictures in the first vertical row from the left are phase contrast pictures of the specimens. The pictures in the second vertical row from the left are DAPI fluorescently-stained images taken at an excitation wavelength of 360 nm and a detection wavelength of 460 nm, in which the bright spots correspond to nuclei. The pictures in the third vertical row from the left are FITC fluorescently-stained images taken at an excitation wavelength of 470 nm and a detection wavelength of 525 nm, in which the bright spots correspond to neurofilaments. The pictures in the fourth vertical row from the left are composite pictures of the second row pictures and the third row pictures.

The FITC fluorescently-stained image of the specimen 1 where NGF and β-sitosterol were added to the culture medium is compared with that of the comparative specimen 2 where NGF was added to the culture medium but β-sitosterol was not added thereto. It is known that the fluorescently-stained image of the specimen 1 has a larger number of bright spots than those in the fluorescently-stained image of the comparative specimen 2, that is, a larger number of neurofilaments appeared in the former. From this, it is known that adding β-sitosterol to a culture medium promotes NGF-inductive neural differentiation.

INDUSTRIAL APPLICABILITY

According to the present invention, there can be provided a neurogenesis stimulant at low cost, which can effectively promote formation and extension of neurites in nerve cells. Consequently, using the neurogenesis stimulant of the present invention, there can be provided an inexpensive internal agent that can relive cognitive dysfunction and motor dysfunction to be caused by neurodegenerative disorders or nerve damages. Accordingly, the industrial applicability of the present invention is great.

The invention claimed is:

1. A method for promoting neural differentiation induced by a nerve growth factor, comprising adding the nerve growth factor and a compound having a structure represented by the following formula (1) to a culture medium for stem cells:

Formula (1)

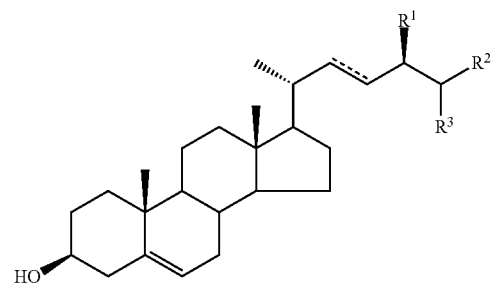

wherein $R^1$ to $R^3$ each independently represent an alkyl group having 1 to 10 carbon atoms, and the broken line means presence or absence of a bond.

\* \* \* \* \*